Figure 1:
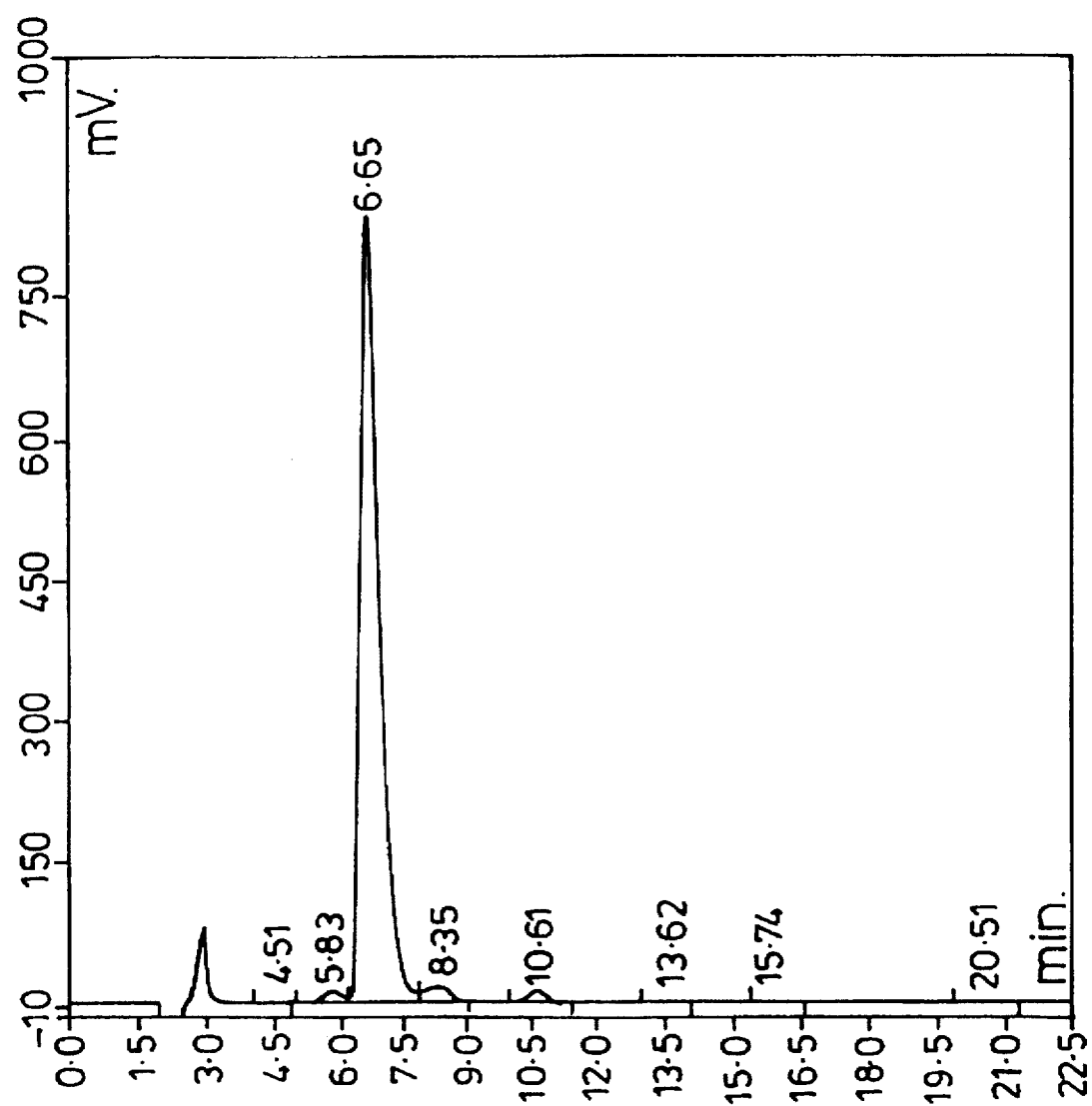

United States Patent [19]

Arvinte

[11] Patent Number: 5,733,874
[45] Date of Patent: Mar. 31, 1998

[54] STABLE DRY POWDERS

[75] Inventor: Tudor Arvinte, Münchenstein, Switzerland

[73] Assignee: Novartis Corp., Summit, N.J.

[21] Appl. No.: 378,225

[22] Filed: Jan. 25, 1995

[30] Foreign Application Priority Data

Jan. 26, 1994 [GB] United Kingdom .................. 9401448

[51] Int. Cl.$^6$ .......................... A61K 38/19; A61K 47/02
[52] U.S. Cl. ................................. 514/12; 514/21
[58] Field of Search ........................... 514/12, 21

[56] References Cited

FOREIGN PATENT DOCUMENTS 0 468 327 A2  7/1991  European Pat. Off. .
    4249766  11/1993  Japan .

OTHER PUBLICATIONS

Degryse et al., "influence of storage conditionsn on the activity of recombinant hirudin", Abstract, *Thrombosis Research* 61: 87–89 (1991).

Johnson et al., "Biochemistry and Genetic Engineering of Hirudin", *Seminars in Thrombosis and Hemostasis*, 15(3) 302–315 (1989).

*Primary Examiner*—Cecilia J. Tsang
*Assistant Examiner*—P. Lynn Touzeau
*Attorney, Agent, or Firm*—Henry P. Nowak; Gregory D. Ferraro

[57] ABSTRACT

The present invention provides a freeze dried pharmaceutical composition comprising hirudin and a water-soluble salt of calcium and/or magnesium.

10 Claims, 1 Drawing Sheet

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 62 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:1:

```
Val Val Tyr Thr Asp Cys Thr Glu Ser Gly Gln Asn Leu Cys Leu Cys
 1               5                  10                  15
Glu Gly Ser Asn Val Cys Gly Gln Gly Asn Xaa Cys Ile Leu Gly Ser
            20                  25                  30
Asp Gly Glu Xaa Asn Gln Cys Val Thr Gly Glu Gly Thr Pro Xaa Pro
        35                  40                  45
Gln Ser Xaa Asn Asp Gly Asp Phe Glu Glu Ile Pro Glu Xaa
        50                  55                  60
```

( 2 ) INFORMATION FOR SEQ ID NO:2:

( i ) SEQUENCE CHARACTERISTICS:
    ( A ) LENGTH: 65 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:2:

```
Leu Thr Tyr Thr Asp Cys Thr Glu Ser Gly Gln Asn Leu Cys Leu Cys
 1               5                  10                  15
Glu Gly Ser Asn Val Cys Gly Gln Gly Asn Lys Cys Ile Leu Gly Ser
            20                  25                  30
Asp Gly Glu Lys Asn Gln Cys Val Thr Gly Glu Gly Thr Pro Lys Pro
        35                  40                  45
Gln Ser His Asn Asp Gly Asp Phe Glu Glu Ile Pro Glu Glu Tyr Leu
        50                  55                  60
Gln
```

( 2 ) INFORMATION FOR SEQ ID NO:3:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:3:

```
Ile Thr Tyr Thr Asp Cys Thr Glu Ser Gly Gln Asn Leu Cys Leu Cys
 1               5                  10                      15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Xaa Pro
        35                  40                  45

Glu Ser His Asn Asn Gly Asp Phe Glu Glu Ile Pro Glu Glu Xaa Leu
    50                  55                  60

Gln
65
```

( 2 ) INFORMATION FOR SEQ ID NO:4:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:4:

```
Val Val Tyr Thr Asp Cys Thr Glu Ser Gly Gln Asn Leu Cys Leu Cys
 1               5                  10                      15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Asn Pro
        35                  40                  45

Glu Ser His Asn Asn Gly Asp Phe Glu Glu Ile Pro Glu Glu Tyr Leu
    50                  55                  60

Gln
65
```

( 2 ) INFORMATION FOR SEQ ID NO:5:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:5:

```
Ile Thr Tyr Thr Asp Cys Thr Glu Ser Gly Gln Asn Leu Cys Leu Cys
 1               5                  10                      15
```

| | | | | | | | | | | | | | | |
|---|---|---|---|---|---|---|---|---|---|---|---|---|---|---|
| Glu | Gly | Ser | Asn 20 | Val | Cys | Gly | Lys | Gly 25 | Asn | Lys | Cys | Ile | Leu 30 | Gly | Ser |
| Asn | Gly | Lys 35 | Gly | Asn | Gln | Cys | Val 40 | Thr | Gly | Glu | Gly | Thr 45 | Pro | Xaa | Pro |
| Glu | Ser 50 | His | Asn | Asn | Gly | Asp 55 | Phe | Glu | Glu | Ile | Pro 60 | Glu | Glu | Xaa | Leu |
| Gln 65 | | | | | | | | | | | | | | | |

STABLE DRY POWDERS

The present invention relates to compositions containing hirudin and in particular to stable powder formulations.

Hirudin, an anticoagulant naturally occurring in leeches (*Hirudo medicinalis*), is not a single polypeptide species but a class of equally acting polypeptides consisting of at least four representatives designated hirudin variant 1 (HV1), hirudin variant 2 (HV2) (cf. European Patent Application No. 158 564) hirudin variant 3 (PA) [cf. PCT-Application No. 86/03493] and "des-(Val)$_2$-hirudin" (cf. European Patent Application No. 158 986). The variants differ in structure from each other by a number of amino acids (especially, the N-terminal sequence of HV1 is Val-Val-Tyr, that of HV2 and of HV3 is Ile-Thr-Tyr and that of "des-(Val)$_2$-hirudin" is Thr-Tyr) but have an accumulation of hydrophobic amino acids at the N-terminus and of polar amino acids at the C-terminus, a tyrosine residue (Tyr$^{63}$) present as sulphate monoester, three disulphide bridges and the anticoagulant activity in common.

In the past few years cDNAs and synthetic genes coding for hirudin variants have been cloned and expressed in microbial hosts. Although the expression products lack the sulphate monoester group at Tyr$^{63}$—and were therefore designated "desulphatohirudins"—they mined out to exhibit approximately the same biological activity as the natural, sulphated hirudins. Desulphatohirudin variant HV1 has been expressed in *Escherichia coli* (European Patent Applications No. 158 564 and 168 342) and in *Saccharomyces cerevisiae* (European Patent Applications No. 168 342, 200 655, 225 633, 252 854 and 341 215). Similarly, desulphatohirudin HV2 has been expressed in *Escherichia coli* (European Patent Applications No. 158 564) and in *Saccharomycescerevisiae* (European Patent Application No. 200 655, PCT-Application No. 86/01224] and des-(Val)$_2$-desulphatohirudin has been expressed in *Escherichia coli* (European Patent Application No. 158 986).

According to the present invention, the term "hirudin" is intended to embrace hirudin, desulphathohirudin, a hirudin variant or a desulphatohirudin variant or a mutant thereof, respectively, described in the literature and in particular a desulphatohirudin compound or a mutant thereof obtainable from a transformed microorganism strain containing DNA which codes for a desulphatohirudin or a mutant thereof. Such desulphatohirudins are, for example, desulphatohirudin variant HV1, HV1 modified (a, b), HV2, HV2 modified (a, b, c), HV3, variants of HV3 and des (Va$_{12}$)-desulphatohirudin.

Preferred desulphatohirudins are those having the formula (SEQ ID NO: 1)

Val Val Tyr Thr Asp Cys Thr Glu Ser Gly Gln Asn Leu Cys Leu Cys (I)
1               5                    10                      15

Glu Gly Ser Asn Val Cys Gly Gln Gly Asn Xaa Cys Ile Leu Gly Ser
                20                  25                  30

Asp Gly Glu Xaa Asn Gln Cys Val Thr Gly Glu Gly Thr Pro Xaa Pro
           35                  40                  45

Gln Ser Xaa Asn Asp Gly Asp Phe Glu Glu Ile Pro Glu Xaa
      50                  55                  60 in which
a) Xaa at 27, 36 end 47 are each Lys, Xaa at 51 is His and Xaa at 62 is the peptide residue Glu-Tyr-Leu-Gln (HV1), or
b) Xaa at 27 is Ile or Glu and Xaa at 36,47,51 and 62 are as defined in a) (HV1 modified a), or c) Xaa at 36 is Ile or Glu and Xaa at 27, 47, 51 and 62 are as defined in a) (HV1 modified a), or
d) Xaa at 47 is Ile or Glu and Xaa at 27, 36, 51 and 62 are as defined in a) (HV1 modified a) , or
e) Xaa at 51 is Leu or Asp and Xaa at 27, 36, 47 and 62 are as defined in a) (HV1 modified a), or
f) Xaa at 62 is selected from the group consisting of Glu-Tyr, Glu-Tyr-Leu, Glu-Asp-Leu-Gln, Glu-Glu-Leu-Gln, Glu-Tyr-Lys-Arg, Glu-Asp-Lys-Arg, Glu-Lys-Leu-Gln, Ser-Phe-Arg-Tyr, Trp-Glu-Leu-Arg, Glu-Tyr-Leu-Gln-Pro and Glu-Tyr-Leu-Gln-Arg and Xaa at 27, 36, 47 and 51 are as defined in a) (HV1 modified b), or having the formula (SEQ ID NO: 2)

Leu Thr Tyr Thr Asp Cys Thr Glu Ser Gly Gln Asn Leu Cys Leu Cys (II)
1               5                    10                      15

Glu Gly Ser Asn Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
           35                  40                  45

Gln Ser His Asn Asp Gly Asp Phe Glu Glu Ile Pro Glu Glu Tyr Leu
      50                  55                  60

Gln
65 or having the formula (SEQ ID NO: 3)

Ile Thr Tyr Thr Asp Cys Thr Glu Ser Gly Gln Asn Leu Cys Leu Cys (III)
1               5                    10                      15

Glu Gly Ser Asn Val Cys Gly Lys Gly Asn Lys Cys Ile Leu Gly Ser
                20                  25                  30

Asn Gly Lys Gly Asn Gln Cys Val Thr Gly Glu Gly Thr Pro Xaa Pro
           35                  40                  45

Glu Ser His Asn Asn Gly Asp Phe Glu Glu Ile Pro Glu Glu Xaa Leu
      50                  55                  60

Gln
65 in which a) Xaa at 47 is Asn and Xaa at 63 is Tyr (HV2), or
b) Xaa at 47 is Lys, Arg or His and Xaa at 63 is Tyr (HV2 modified a), or
c) Xaa at 63 is Glu or Asp and Xaa at 47 is Asn (HV2 modified b), or having the formula (SEQ ID NO: 4)

Val Val Tyr Thr Asp Cys Thr Glu Ser Gly Gln Asn Leu Cys Leu Cys (IV)
1               5                    10                      15

Glu Gly Ser Asn Val Cys Gly Lys Gly Asn Lys Cys Ile Leu Gly Ser
                20                  25                  30

Asn Gly Lys Gly Asn Gln Cys Val Thr Gly Glu Gly Thr Pro Asn Pro
           35                  40                  45

Glu Ser His Asn Asn Gly Asp Phe Glu Glu Ile Pro Glu Glu Tyr Leu
      50                  55                  60

Gln
65 or having the formula (SEQ ID NO: 5)

Ile Thr Tyr Thr Asp Cys Thr Glu Ser Gly Gln Asn Leu Cys Leu Cys (V)
1         5                    10                15
Glu Gly Ser Asn Val Cys Gly Lys Gly Asn Lys Cys Ile Leu Gly Ser
           20                25                  30
Asn Gly Lys Gly Asn Gln Cys Val Thr Gly Glu Gly Thr Pro Xaa Pro
       35                  40                 45
Glu Ser His Asn Asn Gly Asp Phe Glu Glu Ile Pro Glu Glu Xaa Leu
           50              55                 60
Gln
65

HV3 and variants of said HIV3 which are characterised by a shortening of the primary structure by 1 or 2 amino acids at the N-terminus or by 18, 10, 9, 6, 4 or 2 amino acids at the C-terminus.

Particularly preferred desulphatohirudin compounds are those of formula I in which the Xaa groups are as defined under a) or the compound of formula III in which Xaa at 47 is Lys and Xaa at 63 is Tyr.

The most preferred hirudin is desulfatohirudin HV1 having the formula I in which Xaa at 27, 36 and 47 are each Lys, Xaa at 51 is His and Xaa at 62 is the peptide residue Glu-Tyr-Leu-Gln.

The hirudins used in the present invention can be prepared synthetically, e.g. chemically or preferably by recombinant techniques, or by isolation from leeches.

According to the present invention the term "mutant" refers to proteins (muteins) exhibiting antithrombotic activity which differ from native hirudin or desulphathohirudin by simple or multiple mutations (cf. European Patent Applications No. 352 227 and No. 352 228). The DNA coding for said mutants which can be prepared by methods known in the art e.g. site-directed mutagensis, is cloned and expressed in microbial hosts such as *Escherichia coli* and *Saccharomyces cerevisiae*.

The hirudin compounds used in the invention can be in the free form but also in the form of their salts. As they contain free amino group in several amino acid residues, the compounds can be in the form of acid addition salts. Suitable acid addition salts are in particular pharmacologically acceptable salts with conventional therapeutically acceptable acids. Representative inorganic acids are hydrohalic acids (such as hydrochloric acid), and also sulfuric acid, phosphoric acid and pyrophosphoric acid. Representative organic acids are in particular arenesulfonic acids (such as benzenesulfonic or p-toluenesulfonic acid), or lower alkanesulfonic acids (such as methanesulfonic acid), as well as carboxylic acids such as acetic acid, lactic acid, palmitic acid, stearic acid, malic acid, tartaric acid, ascorbic acid and citric acid. As, however, the compound used in the invention also contain free carboxyl groups in several amino acid residues, which carboxyl groups impart acidic character to the entire peptide, they can also be in the form of salts with inorganic or organic bases, e.g. sodium, potassium, calcium or magnesium salts, or also ammonium salts derived from ammonia or a pharmacologically acceptable organic nitrogen-containing base. However, as they contain at the same time free carboxyl groups and free amino groups, they can also be in the form of inner salts. Pharmacologically acceptable salts are preferred.

One problem in developing a dosage form containing hirudin is its poor stability in aqueous solutions and in powder form.

The poor stability can be seen when hirudin is analysed by chromatographic methods, such as reverse phase HPLC (RP-HPLC).

RP-HPLC method: A LiChroCART 125-4 column is used (Merck LiChrospher 100 RP-18 5pm). Solvent A is 0.5% ammoniumacetate in acetonitrile/water (10:90), (v:v); solvent B is 0.5% ammoniumacetate in acetonitrile/water (25:75). The elution is performed at 45° C. using a flow rate of 0.5 ml/min. The binary elution is a linear gradient starting at time zero with 23% solvent B and reaching 46% solvent B after 24 minutes. After 2 min at 70% solvent B the column is equilibrated for 7 rain at 23% solvent B.

A typical chromatogram of recombinant hirudin HV1 (CGP 39393) in water using the RP-HPLC (1 mg/ml hirudin) method is shown in FIG. 1.

BRIEF DESCRIPTION OF DRAWING

In FIG. 1, the relative area of the main peak is 95.15%. Storage of hirudin in water at room temperature results in an increase of by products with time. This shows itself by a decrease in the area of the main peak and an increase in the area of the small peaks. The changes which occur can be accelerated by using temperature stress experiments i.e. by storage at elevated temperatures.

We have now found that magnesium or calcium salts can be used to increase the stability of hirudin.

Accordingly the present invention provides a freeze dried pharmaceutical composition comprising hirudin and a water soluble salt of calcium and/or magnesium.

Suitable water soluble salts include magnesium sulphate, magnesium chloride and calcium chloride.

The composition of the invention may be produced by forming an aqueous solution of the ingredients and then freeze drying it in a conventional manner. It is important that the composition is made by freeze drying a solution, simply mixing the dry ingredients has no effect on the stability.

The molar ratio of the metal ion (magnesium and/or calcium) to that of hirudin may be up to 40:1, preferably between 4:1 and 20:1, more preferably between 8:1 and 16:1, for instance 10:1 or greater.

If desired a sugar may also be included in the composition.

Suitable sugars include mannitol, trehalose, sucrose, sorbitol, fructose, glucose, maltose, lactose and dextran. The preferred sugars are mannitol and trehalose.

The amount of sugar in the solution before freeze drying may be such as to produce a concentration of from 5 to 50% (w/v) and preferably from 5 to 20% (w/v). The solution before freeze drying is preferably isotonic.

The pH of the solution before freeze drying may be from 4 to 9, preferably from 7 to 8.

The concentration of hirudin in the solution before freeze drying may be from 0.1 to 500 mg/ml, preferably from 20 to 80 mg/ml.

The freeze dried product is stable for long periods of time without the need for refrigerated storage. In addition, after the product has been redissolved in water, the resulting solution is also stable for long periods e.g. 2 to 3 weeks, although the stability in solution is not as good as the stability of the freeze dried powder.

The solutions made by redissolving the freeze dried product may be used in the production of standard ampoules, pre-filled syringes, or multi-administration systems. The solutions may of course also be used immediately for administration.

The invention is illustrated by the following Examples, in which the percentages given are by weight.

EXAMPLE 1

Aqueous solutions of recombinant desulphatohirudin HV1 (CGP 39393 from Ciba-Geigy) are produced by dissolving it in water or 150 m molar solutions of the salts given in Table 1 below. The pH varied from 4.12 to 4.31. In each case the concentration of hirudin is 30mg/ml.

The solutions are freeze dried and stored at 46° C. At different times, samples are dissolved in water to 1 mg/ml hirudin and the main peak measured by RP-HPLC. The results obtained are given in Table 1 below.

TABLE 1

| System | % Main Peak Area After | | | | |
|---|---|---|---|---|---|
|  | 11 Days | 18 Days | 26 Days | 34 Days | 48 Days |
| Water | 84.3 | 83.5 | 81.9 | 81.2 | 75.4 |
| 1.43% $MgCl_2$ | 95.0 | 96.3 | 95.6 | 94.9 | 91.5 |
| 1.67% $CaCL_2$ | 95.5 | 96.2 | 96.4 | 95.8 | 93.5 |
| 1.8% $MgSO_4$ | 94.2 | 94.2 | 93.2 | 92.9 | 91.2 |

It can be seen that the stability is maintained at a high level even when stored for extended periods at 46° C.

EXAMPLE 2

Aqueous solutions of recombinant desulphatohirudin HV1 (CGP 39393 from Ciba-Geigy) are made by dissolving it in different salt solutions as follows.

$MgCl_2$–120 mMol (1.14%)
$CaCl_2$–120 mMol (1.33%)
$MgSO_4$–287 mMol (3.46%)

In each case the osmolarity is about 300 and the pH is adjusted to about 7 by adding NaOH.

The solutions are freeze dried the resulting powders stored at 79° C. After a certain storage time a sample is redissolved in water to 1 mg/ml hirudin and the main peak measured by RP-HPLC. The results obtained are given in Table 2 below.

TABLE 2

| System | % Main Peak Area After | | | |
|---|---|---|---|---|
|  | 1 Day | 4 Days | 11 Days | 22 Days |
| Water | 78.0 | 59.2 | 50.9 | 43.6 |
| $MgCl_2$ | 95.7 | 95.0 | 85.9 | 83.9 |
| $CaCl_2$ | 96.0 | 97.0 | 89.3 | 90.1 |
| $MgSO_4$ | 95.9 | 92.2 | 80.5 | 83.9 |

It can be seen that the products are stable even when stored at 79° C.

EXAMPLE 3

Aqueous solutions of recombinant desulphatohirudin HVI (CGP 39393 from Ciba-Geigy) are made by dissolving it in water and in mixtures formed from an isotonic $CaCl_2$ solution (120 mM) and an isotonic mannitol solution (5%). In each case the concentration of hirudin is 30 mg/ml.

The solutions are freeze-dried and the resulting powders stored at 79° C. After a certain storage time a sample is redissolved in water to 1 mg/ml hirudin and the main peak area measured by RP-HPLC. The results obtained are given in Table 3 below.

TABLE 3

| System | | % Main Peak Area After | |
|---|---|---|---|
| Mannitol | $CaCl_2$ | 1 Day | 20 Days |
| — | water | — | 76.3 | 42.2 |
| — | 1.3% (120 mM) | 96.1 | 90.7 |
| 1% (55 mM) | 1.04% (96 mM) | 94.5 | 86.9 |
| 2% (110 mM) | 0.78% (72 mM) | 94.1 | 84.2 |
| 3% (164 mM) | 0.52% (48 mM) | 94.3 | 87.2 |
| 4% (219 mM) | 0.26% (24 mM) | 93.8 | 86.3 |

EXAMPLE 4

Aqueous solutions of recombinant desulphatohirudin HVI (CGP 39393 from Ciba-Geigy) are made by dissolving it in water and in mixtures formed from an $MgCl_2$ solution (150 mM) and an isotonic mannitol solution (5%). In each case the concentration of hirudin is 30 mg/ml and the pH is about 7.3–7.4.

The solutions are freeze-dried and the resulting powders stored at 76° C. After a certain storage time a sample is redissolved in water to 1 mg/ml hirudin and the main peak area measured by RP-HPLC. The results obtained are given in Table 4 below.

TABLE 4

| System | | % Main Peak Area After | |
|---|---|---|---|
| Mannitol | $MgCl_2$ | 2 Days | 6 Days |
| — | water | — | 76.3 | 42.2 |
| — | 1.3% (120 mM) | 96.1 | 90.7 |
| 2.5% (91.67 mM) | 0.71% (75 mM) | 92.6 | 93.0 |
| 3% (110 mM) | 0.57% (60 mM) | 94.0 | 92.1 |
| 3.5% (164 mM) | 0.43% (45 mM) | 93.9 | 92.5 |
| 4% (219 mM) | 0.29% (30 mM) | 92.2 | 90.7 |
| 4.5% (246 mM) | 0.14% (15 mM) | 91.1 | 87.0 |

EXAMPLE 5

As aqueous solution of recombinant desulphatohirudin HVI (CGP 393939 from Ciba-Geigy) is made by dissolving it in a solution containing 0.52% (48 mM) $CaCl_2$ and 3% (164 mM) mannitol. The concentration of hirudin is 30mg/ml. The solution has a pH of 4.3. Half of this solution has the pH adjusted to 7.4 using NaOH. Both solutions are freeze dried and stored at 46 C. After a certain storage time a sample is redissolved in water to 1 mg/ml hirudin and the main peak area measured by RP-HPLC. The results obtained are given in Table 5 below. They show the beneficial effect of using a pH between 7 and 8 although good results are also shown at pH 4.3.

TABLE 5

| System | % Main Peak Area After | | | | |
|---|---|---|---|---|---|
|  | Fresh | 38 Days | 67 Days | 105 Days | 143 Days |
| 46° C. pH 4.3 | 95.2 | 91.5 | 91.3 | 90.5 | 87.8 |
| 46° C. pH 7.4 | 96.0 | 95.5 | 94.8 | 94.9 | 95.2 |

EXAMPLE 6

To 50 mg/ml aqueous desulphatohirudin HV1 (CGP 39393 from Ciba) is added 0.49% (51.5 mM) magnesium chloride, 0.57% (51.5 mM) calcium chloride and 3.5% of the excipients mannitol, dextran 78 kD or dextran 10 kD, or no extra excipient. The pH is adjusted to 7.4 with sodium hydroxide and the solutions freeze-dried. After certain times at 75C the samples are redissolved in water to 2.5 mg/ml hirudin and the main peak area measured by RP-HPLC. The results in Table 6 show that a mixture of magnesium chloride and calcium chloride can be used with or without a carbohydrate.

TABLE 6

| System | % Main Peak Area After | |
|---|---|---|
| | 5 Days | 20 Days |
| Water (No Mg or Ca) | 59.2 (4 Days) | 42.2 |
| Mannitol | 74.0 | 51.4 |
| Dextran 78 kD | 88.6 | 82.5 |
| Dextran 10 kD | 88.8 | 84.2 |
| No Carbohydrate | 89.0 | 84.1 |

---

I claim:

1. A freeze dried pharmaceutical composition comprising hirudin and a water-soluble salt selected from the group consisting of calcium chloride, magnesium chloride or magnesium sulphate.

2. A composition as claimed in claim 1 in which the molar ratio of water-soluble salt ions to hirudin is up to 40:1.

3. A composition as claimed in claim 1 which also contains a sugar.

4. A composition as claimed in claim 3 in which the sugar is mannitol, trehalose, sucrose, sorbitol, fructose, glucose, maltose, lactose or dextran.

5. A composition as claimed in claim 1 which the hirudin is a desulphatohirudin variant or a mutant thereof.

6. A composition as claimed in claim 5 in which the himdin is desulphatohirudin HV1.

7. A composition as claimed in claim 1 which is obtained by dissolving the ingredients in water and then freeze drying the solution.

8. A composition as claimed in claim 7 in which the pH of the solution before freeze drying is from 4 to 9.

9. A composition as claimed in claim 1 in which the concentration of hirudin in the solution before freeze drying is from 0.1 to 500 mg/ml.

10. A composition as claimed in claim 9 in which the solution before freeze drying is isotonic.

* * * * *